United States Patent [19]

Olsen

[11] Patent Number: 5,501,678
[45] Date of Patent: Mar. 26, 1996

[54] ADAPTER FOR USE IN CONNECTION WITH OSTOMY EQUIPMENT

[75] Inventor: Hans Olsen, Hørsholm, Denmark

[73] Assignee: Coloplast A/S, Denmark

[21] Appl. No.: 199,266

[22] PCT Filed: Aug. 31, 1992

[86] PCT No.: PCT/DK92/00258

§ 371 Date: Feb. 28, 1994

§ 102(e) Date: Feb. 28, 1994

[87] PCT Pub. No.: WO93/04646

PCT Pub. Date: Mar. 18, 1993

[30] Foreign Application Priority Data

Aug. 30, 1991 [DK] Denmark .................. 1529/91

[51] Int. Cl.$^6$ ..................................... A61F 5/44
[52] U.S. Cl. ..................................... 604/344
[58] Field of Search ..................... 604/344, 341, 604/332

[56] References Cited

U.S. PATENT DOCUMENTS

| 4,219,023 | 8/1980 | Galindo . | |
| 4,710,182 | 12/1987 | Bryson . | |
| 4,834,731 | 5/1989 | Nowak et al. | 604/339 |
| 4,973,323 | 11/1990 | Kaczmarek et al. | 604/344 |

FOREIGN PATENT DOCUMENTS 0416397  3/1991  European Pat. Off. .

Primary Examiner—Jerome L. Kruter
Attorney, Agent, or Firm—Ostrolenk, Faber, Gerb & Soffen

[57] ABSTRACT

A convex adapter for use in connection with ostomy equipment comprises a ring-shaped member (10, 15, 18). The ring-shaped member (10, 15, 18) comprises a central, relatively rigid ring (10) with a convex face (12) as well as a peripheral, relatively flexible part (15) extending considerably longer and radially than the relatively rigid ring (10).

13 Claims, 1 Drawing Sheet

ADAPTER FOR USE IN CONNECTION WITH OSTOMY EQUIPMENT

BACKGROUND OF THE INVENTION

The invention concerns a ring-shaped adapter for use in connection with ostomy equipment, the proximal side of said adapter having a convex face which is provided with adhesive by means of which the adapter can be adhered to the skin of a user, a collection bag or a coupling part therefor being adhered to the distal side of said adapter in use.

Below an ostomy patient or an ostomist denotes a person having a colostomy, an ileostomy or a urostomy. In such persons the colon, the ileum or the ureter has been exposed surgically such that the waste products of the body, which are conveyed through these organs, are discharged through an artificial opening and are collected in a collection bag, which is ordinarily adhered to the skin by means of an adhesive plate with an opening surrounding the stoma.

It is frequently seen in ostomy patients that the closest surroundings of the stoma, at a distance of 1–2 cm, are recessed or are positioned in a crater or a cavity with respect to the rest of the skin surface that surrounds the stoma. For such patients it is expedient to use an ostomy appliance where the adhesive surface around its opening for receiving the stoma has a part which protrudes toward the user with a view to enabling the adhesive face of the ostomy equipment to engage and adhere to the skin everywhere in the crater or the cavity. In particular, it is important that the ostomy equipment adheres to the skin as closely to the stoma as possible, and this location is most frequently the one lying deepest. The shape of the forwardly protruding part of the adhesive face may e.g. be domed or conical, and such appliances are known under the designation convex appliances. Throughout the specification the term convex has this broad meaning irrespective of the actual embodiment.

The invention concerns a convex adapter where the proximal side (the side facing toward the patient) has a convex face, and where an ordinary ostomy bag is adhered to the distal side of the adapter (the side facing away from the patient).

EP 416 397 discloses an adapter of the present type which is provided with a layer of adhesive protruding beyond the outer periphery of the ring-shaped, convex member, the adhesive being exposed on the distal side of the adapter so that when coupled with the adhesive plate of the ostomy equipment it will be in direct contact with the adhesive of this plate. The adhesive of the adapter and the adhesive of the ostomy equipment must be compatible here, which puts a limit to the selection of adhesives. Furthermore, an adapter adhered to ostomy equipment cannot be separated later, which makes it impossible to use the adapter for several collection bags.

EP 317 326 describes a convex adapter where a rigid ring on its entire convex side carries an intermediate ring of soft thermoplastic foam adhered to the rigid ring. The intermediate ring carries a layer of adhesive for mounting the adapter on the skin of a user. The foam ring is a cost-increasing component, and attachment by adhesion to the rigid ring makes the manufacturing process more expensive. Such an adapter requires the use of collection bags having a skin-friendly adhesive which is expensive.

SUMMARY OF THE INVENTION

The object of the invention is to provide a universally useful convex adapter which is not vitiated by the above-mentioned drawbacks, but which can be used together with any known type of ostomy equipment, and which even enables use of collection bags with industrial adhesives which are frequently more inexpensive than special medical grade skin adhesives.

This object is achieved by an adapter as stated in claim 1, providing the following advantages over known adapter rings.

Handling of the product is facilitated considerably when the user is to use the product. The user can decide to mount the adapter on the ostomy equipment before this is placed on the user's skin around the stoma. Alternatively, the adapter can first be placed on the skin around the stoma, and then the ostomy bag is fitted on this. Furthermore, the adapter of the invention has just one adhesive face, which, in contrast to two opposed adhesive faces, gives an easier and safer handling.

Owing to the structure of the adapter, its adhesive will not get in contact with the adhesive of the ostomy equipment. Plasticizers, if any, in the adhesives are hereby prevented from migrating or diffusing from one adhesive to the other. This makes it possible to use even widely different adhesives on the adapter and on the ostomy equipment. The adhesive on the adapter and ostomy equipment which gets in contact with the user's skin must be of a special skin-friendly type, but the adapter of the invention makes it possible to use ostomy equipment with any suitable adhesives without special requirements on skin friendliness, because skin contact can be avoided.

Because the adapter of the invention has just one adhesive face, it cannot be mounted wrongly. In adapters having two opposed, adhesive faces, each of which is covered by a protective layer, it is theoretically possible that the user uses the product wrongly.

Since the adhesive of the adapter is always carried by the ring-shaped member and the sheet integrated with it, the adhesive is never completely exposed. The ring-shaped member and the sheets integrated with it always support and carry the adhesive, thus ensuring that the user will not unintentionally tear the adhesive.

Furthermore, a special embodiment of the invention is possible in which controlled release properties are imparted to the distal side of the adapter, so that an adhered ostomy bag can be removed without the convex adapter, placed around a user's stoma, being removed too. When the bag is to be exchanged, the adapter therefore remains on the user's skin, thereby permitting the same adapter to be used for several bags successively.

BRIEF DESCRIPTION OF THE DRAWING

The invention will be described below with reference to the drawing, in which.

DESCRIPTION OF THE PREFERRED EMBODIMENT

Figure 1:
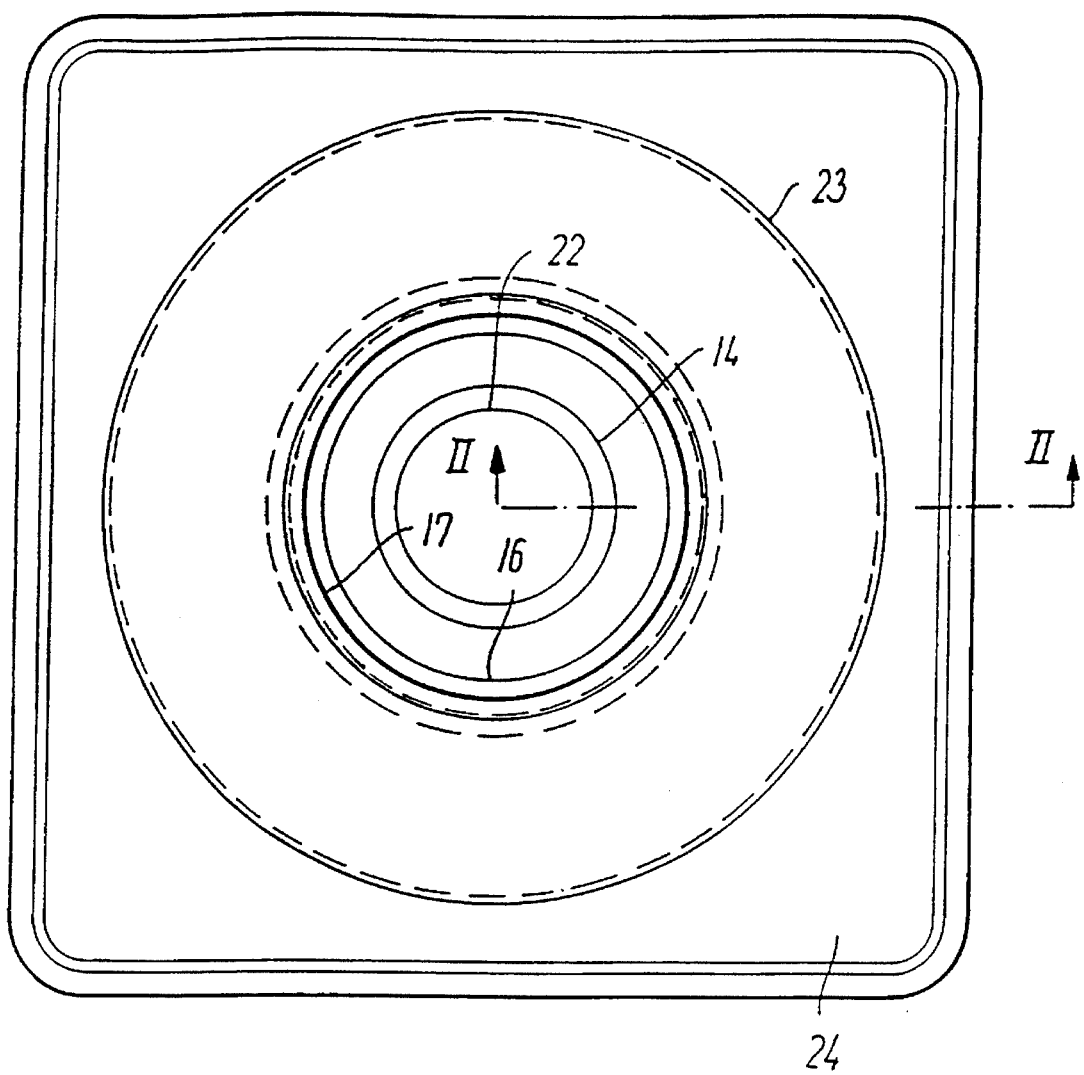
FIG. 1 shows a preferred embodiment of the adapter of the invention.
Figure 2:
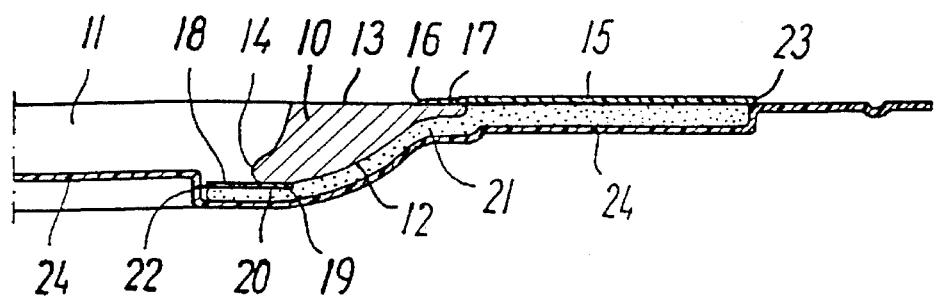
FIG. 2 shows a section through the adapter in FIG. 1 along the line II—II.

The shown adapter has a ring 10 with a central opening 11 and a convex, curved face 12. The convex face 12 is intended to face toward the user, and this side of the adapter is therefore called the proximal side. The opposite side 13 of the ring 10 is flat. The central opening 11 of the ring 10 has a rounded edge 14 near the proximal side of the ring, and distally from the edge 14 the central opening 11 expands toward the flat, distal side 13 of the ring.

A ring-shaped sheet 15 is placed so as to protrude, with its inner periphery 16, inwardly over the flat, distal side 13 of the ring 10, to which it is attached by means of a weld 17 so that the ring 10 and the sheet 15 are contiguous.

A ring-shaped sheet 18 is placed so as to protrude, with its outer periphery 19, inwardly over the convex face 12 of the ring 10, to which it is attached by a weld 20 so that the sheet 18 and the ring 10 are contiguous.

In the preferred embodiment the ring 10, the sheet 15 and the sheet 18 consist of the same material, viz. EVA. The ring 10 has dimensions so that it is relatively rigid with the selected material, i.e. it substantially maintains its shape and dimensions when subjected to normally occurring forces. The sheets 15 and 18 have a thickness so that they are flexible with the selected material, i.e. they are substantially dimensionally stable and are capable of adapting to the contours of the skin and the stoma.

The ring 10 and the sheets 15 and 18 serve as an integrated, ring-shaped member and can optionally be produced by moulding in one process. A layer 21 of a skin-friendly adhesive, which is usually employed for products of this type, is applied on the proximal side of this member 10, 5, 18. A preferred adhesive is described in the DK Patent 157899. Such adhesives usually have a thickness of about 1 mm, while other industrial adhesives typically have a thickness of 0.02–0.03 mm. During the ordinarily long contact with the user's skin the adhesive must be capable of adsorbing the moisture which is constantly released from the skin, and the adhesive must therefore have the mentioned relatively great thickness.

The adhesive 21 extends as an unbroken layer substantially from the inner periphery 22 of the sheet 18 and to the outer periphery 23 of the sheet 15. Adhesives of the type used here may tend to flow or creep, and it may therefore be expedient that the adhesive 21 does not extend right into the inner periphery 22, nor right out to the outer periphery 23, thereby providing an additional margin for compensation for the flow of the adhesive.

The adapter is moreover provided with a removable protective layer 24, which is formed e.g. by vacuum forming so that ideally the protective layer has the same shape as the convex side of the adhesive 21. The protective layer is to offer protection against drying of the adhesive, but also to support the adhesive so that cold flow is limited to the greatest extent possible, and the ideal shape of the adhesive is maintained. The protective layer 24 therefore also covers the inner and outer peripheries of the adhesive. On the side facing toward the adhesive 21 the protective layer is provided with a release coating so that it can easily be removed before the adapter is put to use.

The adhesive plate of the ostomy equipment, with which the adapter of the invention is to be used, may typically have a diameter of 10 cm, which corresponds to the outer diameter of the sheet 15 in a preferred embodiment of the invention. The adhesive plate of the ostomy equipment is then attached by adhesion to the flat, distal side of the adapter, which consists of the flat, distal side 13 of the ring 10 as well as the distal side of the sheet 15. The sheet 15, which is thus positioned between the adhesive 21 of the adapter and the adhesive of the ostomy equipment (not shown), here provides mechanical stabilization of the adhesive layers and protects against migration of plasticizers between the two optionally different adhesives.

It is noted that in the embodiment shown here the adhesives of the ostomy equipment at no time come into direct contact with the user's skin, but only adhere the ostomy equipment to the distal side of the adapter. Here, any adhesive technically suitable for the purpose may be used for the ostomy equipment, without such an adhesive having to possess special medical properties, e.g. in the form of skin-friendliness.

The ostomy equipment (not shown) with which the adapter of the invention is to be used, may be a collection bag with an integrated adhesive plate, or ostomy equipment consisting of two parts which are coupled together in use, one of which carrying an adhesive plate with a coupling part for coupling with the other part of the ostomy equipment which consists of a collection bag with the other part of the coupling. A preferred coupling is described in the International Patent Application PCT/DK90/00192. The part of such an ostomy coupling which is integrated with the adhesive plate may advantageously be integrated with the adapter of the invention, since this coupling part may advantageously be contiguous with the ring 10 and be attached to it by welding.

In use the central opening 11 of the adapter surrounds the user's stoma, which often protrudes somewhat from the surrounding skin and into the central opening 11. The sheet 18 is flexible so that it can yield and conform to the stoma. However, the user often needs to adapt the ostomy equipment to the shape of the stoma, and the user can here cut the sheet 18 and the part of the adhesive 21 positioned across the sheet 18, thereby providing an opening which fits the stoma in the best way possible.

We claim:

1. An adapter for use together with ostomy equipment and comprising a ring-shaped member (10, 15, 18) with a radial extent between an inner periphery (22) and an outer periphery (23) and having a proximal side and a distal surface, said proximal surface having a convex face (12) and on its proximal side a layer of adhesive (21) by means of which the adapter can be adhered to a user's skin, the ring-shaped member (10, 15, 18) comprising a central, relatively rigid ring (10) with the convex face (12) and a peripheral part (15) which is an integrated part of the relatively rigid ring (10), characterized in that the peripheral part (15) is relatively flexible and extends radially considerably further than the relatively rigid ring (10), the peripheral part (15) consisting of a proximal side and a distal side, the proximal side being in contact with the layer (21) of adhesive, and at least as far as the layer of adhesive, the distal side being flat and non-adhesive and being adapted for direct connection with the ostomy equipment.

2. An adapter according to claim 1, characterized in that the peripheral part (15) is an outer flexible sheet which is welded to the central ring (10).

3. An adapter according to claim 2, characterized in that the ring-shaped member (10, 15, 18) comprises an inner relatively flexible sheet (18) which is an integrated part of the relatively rigid ring (10) and extends inwards of the inner periphery of said ring.

4. An adapter according to claim 3, characterized in that the inner relatively flexible sheet (18) is welded to the relatively rigid ring.

5. An adapter according to claim 4 characterized in that the adhesive layer (21) is covered by a removable protective sheet (24).

6. An adapter according to claim 5, characterized in that the protective sheet (24) has a shape which is adapted to the proximal side of the adapter.

7. An adapter according to claim 6, characterized in that the relatively rigid ring (10) has a central opening (11) with a rounded edge (14) near the proximal side of the ring (10), and distally from edge (14), the central opening (11) expands toward a flat, distal side (13) of the ring.

8. An adapter according to claim 1, characterized in that the ring-shaped member (10, 15, 18) comprises an inner relatively flexible sheet (18) which is an integrated part of the relatively rigid ring (10) and extends inwards of the inner periphery of said ring.

9. An adapter according to claim 8, characterized in that the inner relatively flexible sheet (18) is welded to the relatively rigid ring.

10. An adapter according to claim 1, characterized in that the adhesive layer (21) is covered by a removable protective sheet (24).

11. An adapter according to claim 10, characterized in that the protective sheet (24) has a shape which is adapted to the proximal side of the adapter.

12. An adapter according to claim 1, characterized in that the relatively rigid ring (10) has a central opening (11) with a rounded edge (14) near the proximal side of the ring (10), and distally from edge (14), the central opening (11) expands toward a flat, distal side (13) of the ring.

13. An adapter according to claim 1, characterized in that the peripheral part (15) is made of a material impermeable to substances harmful to the skin to thereby provide a barrier between such substances and the layer of the adhesive.

* * * * *